(12) United States Patent
Sahu et al.

(10) Patent No.: US 11,219,701 B1
(45) Date of Patent: Jan. 11, 2022

(54) ULTRAVIOLET C-BAND AIR SANITIZER

(71) Applicant: Science Cadets, Inc., San Jose, CA (US)

(72) Inventors: Anwesh Patnaik Sahu, San Jose, CA (US); Saroj Kumar Sahu, San Jose, CA (US)

(73) Assignee: Science Cadets, Inc., San Jose, CA (US)

( * ) Notice: Subject to any disclaimer, the term of this patent is extended or adjusted under 35 U.S.C. 154(b) by 61 days.

(21) Appl. No.: 16/944,531

(22) Filed: Jul. 31, 2020

(51) Int. Cl.
*A61L 9/20* (2006.01)
*G01N 21/64* (2006.01)
*G01J 1/42* (2006.01)

(52) U.S. Cl.
CPC .................. *A61L 9/20* (2013.01); *G01J 1/429* (2013.01); *G01N 21/6428* (2013.01); *A61L 2209/111* (2013.01); *A61L 2209/12* (2013.01); *A61L 2209/14* (2013.01); *G01N 2021/6439* (2013.01); *G01N 2201/062* (2013.01)

(58) Field of Classification Search
CPC ......... G01J 1/429; A61L 9/20; G01N 21/6428
See application file for complete search history.

(56) References Cited

U.S. PATENT DOCUMENTS

| | | | |
|---|---|---|---|
| 4,017,736 A | 4/1977 | Ross | |
| 5,837,207 A | 11/1998 | Summers | |
| 7,459,694 B2 | 12/2008 | Scheir et al. | |
| 7,626,187 B2 * | 12/2009 | Younts | A61L 2/02 250/455.11 |
| 8,226,887 B2 | 7/2012 | Harmon et al. | |
| 9,265,850 B2 | 2/2016 | Davis et al. | |
| 9,327,047 B1 | 5/2016 | Lichtblau | |
| 9,370,600 B1 * | 6/2016 | DuPuis | A61L 9/20 |
| 2011/0138905 A1 * | 6/2011 | Kim | G01K 13/00 73/290 V |
| 2019/0046812 A1 * | 2/2019 | Harlan | A61C 19/004 |

* cited by examiner

*Primary Examiner* — Michael C Bryant
(74) *Attorney, Agent, or Firm* — Chen-Chi Lin (57) ABSTRACT

An air sanitizer generates active airflow utilizing ultraviolet spectrum of light in the UV-C band (200-280 nm). The source of the UV-C is an array of light emitting diodes (LED) that shine the UV-C down a housing of the air sanitizer. A fan draws the contaminated air into the housing. The contaminated air is sanitized by the UV-C light inside the housing and is expelled through apertures at the other end of the housing. Leaking of the potential harmful UV-C light outside of the housing is eliminated by an optical baffle covering the apertures. The electronics design for the air sanitizer contains an LED driver with temperature compensation to optimize the service life of the LEDs. A UV light flux detector facing the UV-C LEDs measures the relative reduction of UV light flux over time and reports the efficacy of the UV-C LEDs during the operation of the air sanitizer.

22 Claims, 9 Drawing Sheets

ULTRAVIOLET C-BAND AIR SANITIZER

CROSS-REFERENCE TO RELATED PUBLICATIONS

The disclosure made in U.S. Pat. No. 7,459,694 to Scheir et al.; U.S. Pat. No. 7,626,187 to Younts; U.S. Pat. No. 8,226,887 to Harmon et al.; U.S. Pat. No. 9,265,850 to Davis et al.; U.S. Pat. No. 4,017,736 to Ross; U.S. Pat. No. 5,837,207 to Summers; and U.S. Pat. No. 9,327,047 to Lichtblau are hereby incorporated by reference.

FIELD OF THE INVENTION

This invention relates generally to an air sanitizer. More particularly, the present invention relates to an ultraviolet C-band air sanitizer to reduce germ (such as virus and bacteria) and pest levels in enclosed spaces, such as homes, offices, factories, vehicles, airplanes and green-houses; a process to control temperatures of ultraviolet C light emitting diodes (UV-C LEDs); and a method to monitor the degradation of the UV-C LEDs.

INTRODUCTION

Ultraviolet light in the C-band (UVC, 200-280 nm) with an adequate dosage has been known to sterilize contaminated surfaces. For instance, in U.S. Pat. No. 7,459,694 to Scheir et al., there is disclosed a movable germicidal system comprising lamps for disinfecting the walls of a room. In another instance, in U.S. Pat. No. 7,626,187 to Younts, there is disclosed a handheld device to disinfect neutralize undesirable elements on surfaces of different articles. In another instance, in U.S. Pat. No. 8,226,887 to Harmon et al., there is disclosed a mobile disinfectant device using UV light guided by a movement sensor. In another instance, in U.S. Pat. No. 9,265,850 to Davis et al., there is disclosed a flexible want that emits UV light to sanitize contaminated surfaces.

As may be noted above, in recent years, much attention has been given to inventing devices to sanitize surfaces.

Many germs can be air-borne and can stay active in ambient air for hours, thereby triggering air-borne transmission of diseases and infections in humans, animals, and plants. It is therefore useful to have a device that can reduce or eliminate the load of air-borne germs by sanitizing the air, especially in contained environments, such as homes, offices, factories, vehicles, airplanes and green-houses.

Many inventions have addressed the problem of sanitizing air with UV light, especially while the air is being guided through a duct. However, they do not specifically teach the efficacy of the UV-C band (200-280 nm), which is effective for neutralizing the germs. Longer wavelength UV bands, such as UV-A (in wavelength range 320-400 nm) and UV-B (in wavelength range 280-320 nm), are not effective for neutralizing a vast majority of germ types.

For instance, in U.S. Pat. No. 4,017,736 to Ross, there is disclosed an air purification system, where sub-micron filtered air is flown through a housing while light from UV lamps is shone through the air. Such UV lamps are primarily mercury fluorescent lamps and have high power requirements, have low service life and have high maintenance costs, and also do not optimize their optical power in UV-C band.

In another instance, in U.S. Pat. No. 5,837,207 to Summers, there is disclosed a portable germicidal air filter, where light from a UV lamp is dynamically collimated and distributed in an air volume with a system of moving concave mirrors and lenses. While U.S. Pat. No. 5,837,207 to Summers does not teach the efficacy of UV-C band, it is worth mentioning that the UV-C light would be largely absorbed by most common materials used for the system of mirrors and lenses and therefore would not be available for the sanitization purposes.

In another instance, in U.S. Pat. No. 9,327,047 to Lichtblau, there is disclosed an air decontamination system, which has a similar construction as aforementioned art in U.S. Pat. No. 4,017,736 to Ross, but has two improvements—it particularly cites the efficacy of UV-C band and provides means prevent the leakage of UV-C radiation to outside environment thereby addressing the safety concerns of UV-C radiation.

Shortcomings in the Prior Art

Because air is a medium of extremely low density, the reaction cross-section of UV light with germ particles in the air is exceedingly small. Therefore, much of the UV light generated by the lamps is absorbed by the walls of the housing before hitting the germs. This requires the lamps to have enormous flux to be effective in sanitizing contaminated air. It results in high power consumption, and management of large amount of heat generated by these powerful lamps.

Because UV-C spectrum is unsafe for human eye and skin, any part of the UV light generated cannot be allowed to escape the sanitization volume. The prior arts that teach using UV light in sanitizing surfaces usually fail to caution against this danger and generally fail to provide a safe apparatus from this perspective.

Most UV lamps, including mercury bulbs and UV-LEDs, lose their optical output gradually with age. Less optical output results in lost efficacy in sanitization. It is therefore essential to monitor the intensity of the UV light inside the sanitizing housing to determine the age of the light generator, otherwise a false sense of security would prevail by assuming that the UV light is potent enough for sanitization. The prior arts in this field generally do not teach a method to monitor the age of the UV lamp or UV-C LED.

BACKGROUND OF THE INVENTION

An object of the present disclosure is to provide an air sanitization device using highly efficient UV-C LEDs with optimal usage of the photon flux by using efficient internal UV reflectors.

A further object of the present disclosure is to provide a method to monitor the degradation of the UV light so that the efficacy of the sanitization can be known in real time and replacement of the UV-C LEDs can be done at an appropriate time.

A further object of the present disclosure is to provide a method to contain the UV-C radiation within the device volume and prevent it from leaking to the outside environment.

A further object of the present disclosure is to provide a method for power and thermal management of the UV-C LEDs so that their lifetime is increased.

SUMMARY OF THE INVENTION

An array of UV-C LEDs is mounted on a PCB which is thermally mounted on a heatsink. The heatsink is mounted on one side of a housing. A temperature sensor is provided on the PCB or the heat sink. A fan draws external air into the housing while cooling the heatsink. An electronic circuit drives the fan and the UV-C LEDs to a desired power level limited by the safe operating temperature. Air travels from the side containing the fan through the housing and is expelled through small apertures on the other end of the housing, while being sanitized by the UV-C light emitted by the UV-C LEDs. The sanitizing photon flux is maximized by attaching sheets of a UV-C reflector material on the inside walls of the housing. Apertures through which the air is expelled are covered by a UV-C absorbing optical baffle, which lets the air through, but substantially blocks the UV-C light falling on them. The apertures themselves are geometrically narrowed and their internal walls are coated with UV-C absorbing paint so that any stray UV-C photons are substantially absorbed, preventing them from escaping to outside the housing. A UV-C flux detector is placed facing the flux of UV-C LEDs. The detector monitors the amount of flux of UV-C LEDs and therefore detects and reports any reduction of flux over time.

DETAILED DESCRIPTION OF THE INVENTION

Figure 1:
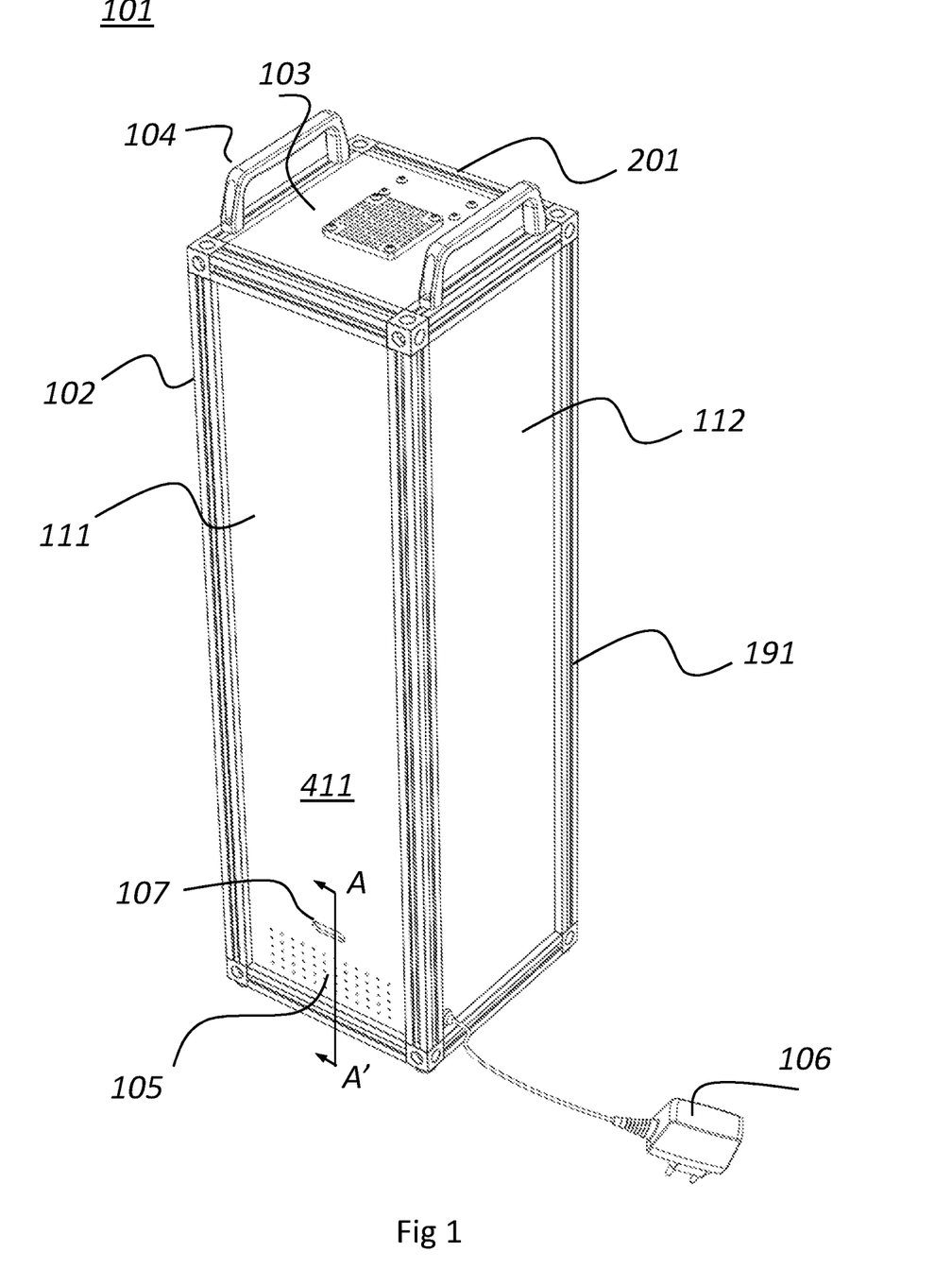
FIG. 1 shows an external perspective view of an air sanitizer in examples of the present disclosure

FIG. 1 shows an external perspective view of an air sanitizer 101 in examples of the present disclosure. The air sanitizer 101 comprises a housing 102, a heatsink 301 of FIG. 3, a printed circuit board (PCB) 305 of FIG. 3, an external power supply 106, an ultraviolet C light emitting diode (UV-C LED) assembly 103 comprising a plurality of UV-C LEDs 304 of FIG. 3, one or more temperature sensors 310 of FIG. 3 (also referred to as thermistor), an electronic circuit, a fan assembly 303 of FIG. 3, a layer of UV-reflective material 401, 403, or 415 of FIG. 4 (also referred to as reflector), one or more (air expelling) apertures 105, one or more UV-blocking optical baffles 402 of FIG. 4 (also referred to as UV-absorbing optical baffles), and an optical flux meter system 414 of FIG. 4 (also referred to as UV-C flux detector). The housing 102 comprises carrying handles 104 and a viewing port 107.

Figure 3:
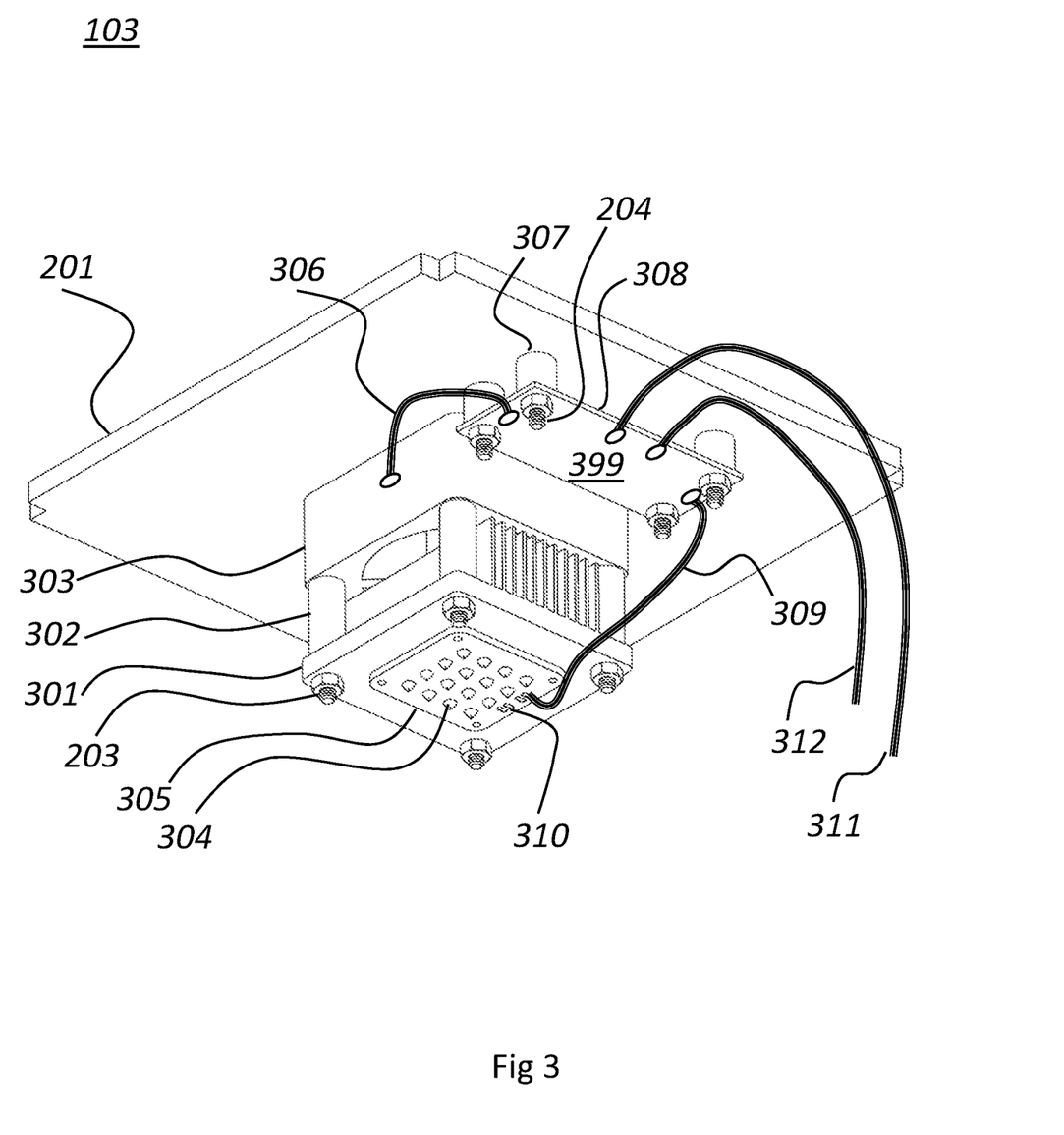
FIG. 3 shows a bottom view of the UV-C LED assembly of FIG. 2 in examples of the present disclosure.

In examples of the present disclosure, the one or more apertures 105 are built into the walls of the housing 102. The PCB 305 is attached to the heatsink 301. The plurality of UV-C LEDs 304 are attached to the PCB 305. The one or more temperature sensors 310 monitor temperature of the heatsink 301 or temperature of the PCB 305. The electronic circuit supplies and controls electrical power to the plurality of UV-C LEDs 304 based on a predetermined optical power level and temperature output values of the one or more temperature sensors 310, and reporting a status of the air sanitizer 101 to a user. The fan assembly 303 draws external air into the housing 102 for cooling the heatsink 301. The layer of UV-reflective material 401, 403, or 405 facilitates a plurality of reflections of UV-C light so as to improve utilization of the UV-C light. The one or more apertures 105 are at a downstream of the housing 102 so as to expel sanitized air. The one or more UV-blocking optical baffles 402 cover the one or more apertures 105.

The UV-C LEDs typically have a spectral distribution spanning into UV-A band, UV-B band, and UV-C band. UV-C band is more effective in disinfecting than UV-B band. UV-B band is more effective in disinfecting than UV-A band. In one example, the plurality of UV-C LEDs 304 have at least 20% of optical power of emission spectrum with wavelength less than 280 nanometers (in UV-C band). In another example, the plurality of UV-C LEDs 304 have at least 50% of optical power of emission spectrum with wavelength less than 280 nanometers.

In examples of the present disclosure, the housing 102 is made of beams 191 of T-slot 2020 standard aluminum hardware and acrylic plates. In examples of the present disclosure, the carrying handles 104 are molded out of ABS plastic and fastened to the T-slot 2020 beams 191 of the housing 102. In examples of the present disclosure, the one or more apertures 105 and the viewing port 107 are disposed on a same acrylic wall 411 (also refers to as a plate) of the housing 102. In examples of the present disclosure, the external power supply 106 is a wall wart that converts the wall AC power to a 12V DC level. The 12V DC power is provided by a power cable into the housing 102 for electronic circuits and devices located within the housing 102.

Figure 2:
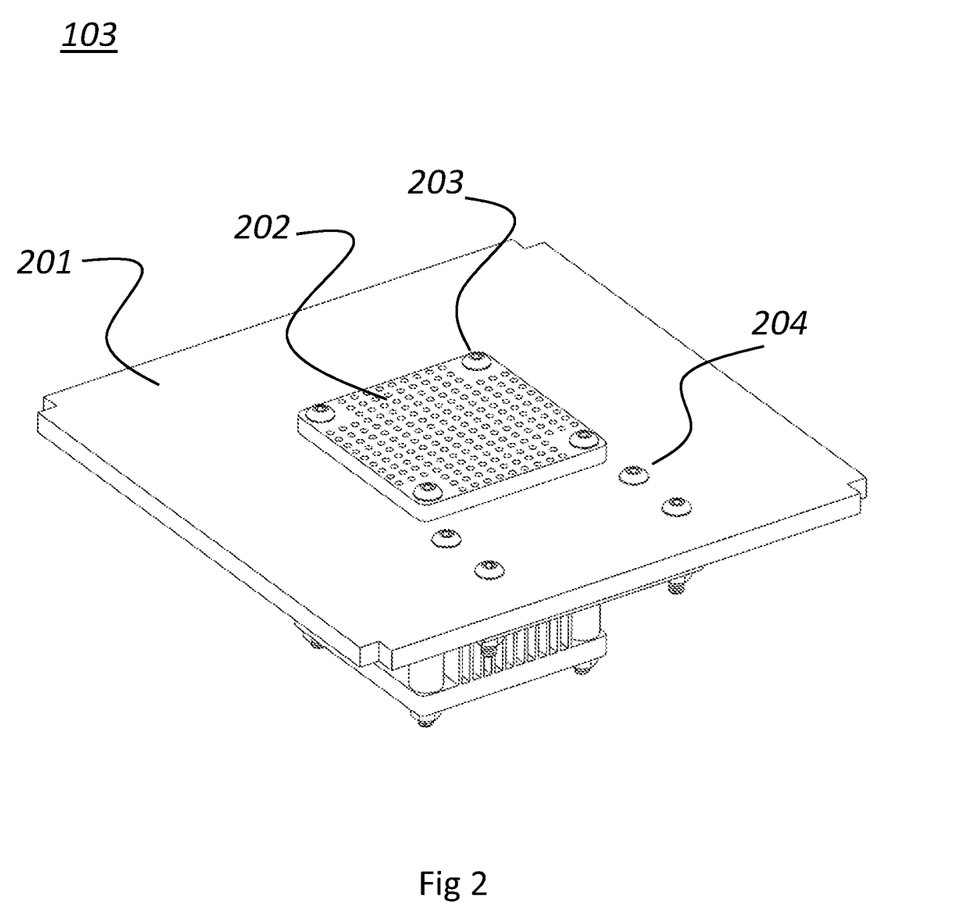
FIG. 2 shows a top view of a UV-C LED assembly in examples of the present disclosure.

In examples of the present disclosure, the UV-C LED assembly 103 incorporates a ceiling wall 201 of the housing 102. Its function is to draw external air into the housing and provide controlled UV-C LED light for sanitization.

Sanitized air is expelled from the housing 102 via the one or more apertures 105 on the wall(s) 411. The one or more apertures 105 are designed such that no leakage flux of UV-C photons escapes outside of the housing 102.

Figure 4:
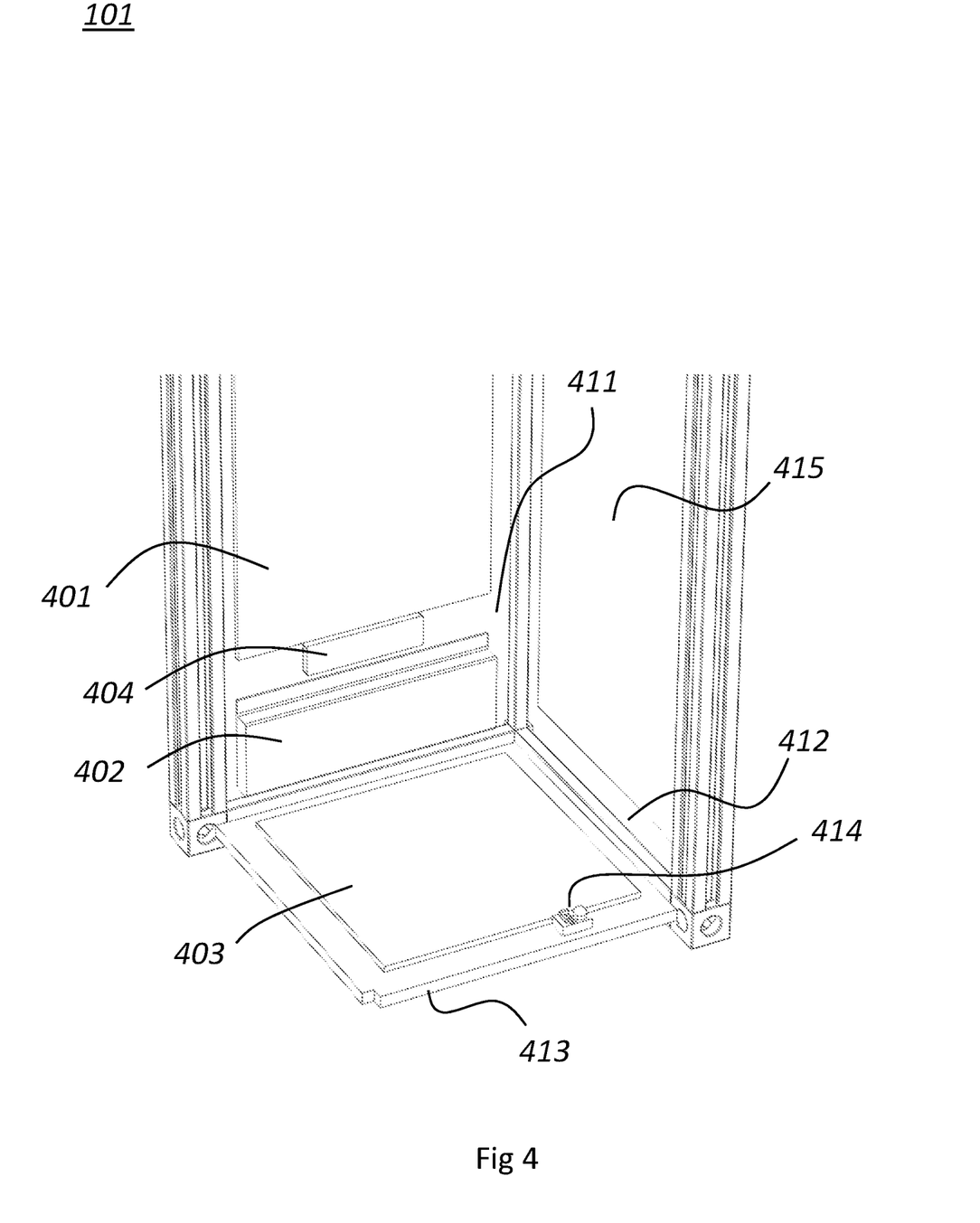
FIG. 4 shows a partial, internal view of a housing in examples of the present disclosure.

In examples of the present disclosure, the viewing port 107 is an oval shaped aperture of dimension 15 mm×8 mm on one of the walls 411 of the housing 102, blocked by a fluorescent and translucent plate 404 of FIG. 4 on the inside wall to visually indicate the presence of UV-C light inside the housing 102 as a safety and operational indication.

FIG. 2 shows a top view of the UV-C LED assembly 103 in examples of the present disclosure. The UV-C LED assembly 103 comprises a PCB 305 of FIG. 3 containing a plurality of UV-C LEDs 304, a heatsink 301 of FIG. 3, a fan assembly 303 of FIG. 3, a replaceable air filter 202 (also referred to as dust filter), and an electronic board 308 of FIG. 3 containing an electronic circuit 399. Screws 203 hold together a ceiling wall 201 of the housing 102, the replaceable air filter 202 and other components to be described in the description of FIG. 3 below. Screws 204 hold together the ceiling wall 201 and the electronic board 308 to be described in FIG. 3 below.

In examples of the present disclosure, the replaceable air filter 202 is a standard part used in electronics venting applications. In examples of the present disclosure, the replaceable air filter 202 comprises a plastic holder with a replaceable open cell foam. For example, the part number 19155K3 manufactured by McMaster-Carr (McMaster.com) may be used for the replaceable air filter 202.

FIG. 3 shows a bottom view of the UV-C LED assembly 103 of FIG. 2 in examples of the present disclosure. In addition to the ceiling wall 201 and the replaceable air filter 202, the screws 203 hold together a fan assembly 303 and a heatsink 301, with spacers 302. In one example, up to 16 UV-C LEDs 304 are mounted in a 4×4 array on an aluminum PCB 305 which is mounted on the heatsink 301 with a thermal interface material. The PCB 305 is further restrained mechanically to the heatsink 301 with screws.

Figure 9:
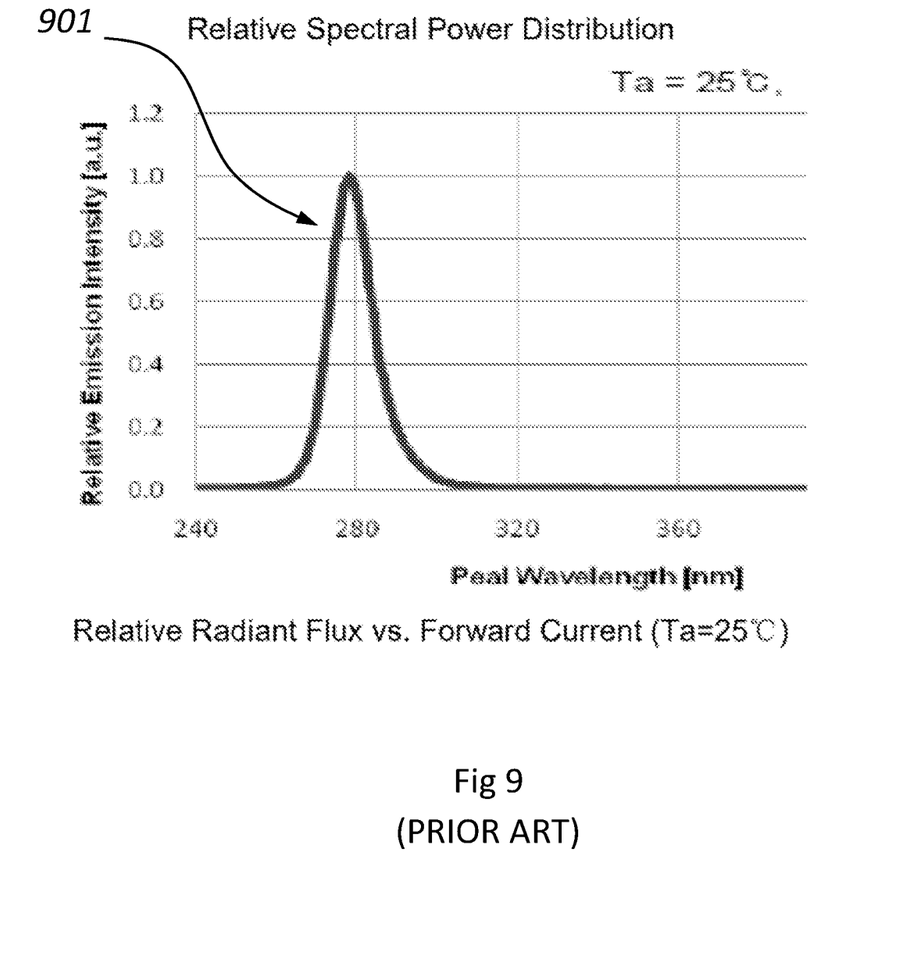
FIG. 9 depicts a spectral distribution of UV-C LEDs in examples of the present disclosure.

In examples of the present disclosure, the plurality of UV-C LEDs 304 may be sourced from the part number of IN-C33DTDU1 of Inolux (inolux-corp.com). The relative spectral power distribution 901 of IN-C33DTDU1 of Inolux is shown in FIG. 9. More than 50% of the total emission is in the wavelength between 240 nm and 280 nm, which is in the UV-C band.

In examples of the present disclosure, the fan assembly 303 is a brushless DC type and may be sourced from the part number AUB0812HH-A of Delta Electronics (deltaww.com). Maximum airflow for AUB0812HH-A of Delta Electronics is 42.4 CFM (1.19 m$^3$/min) and static pressure is 0.207 inch H$_2$O (51.6 Pa). At a desired airflow of at least 10 CFM through the housing 102, the pressure drop in through the air sanitizer is about 0.1 inch H$_2$O. This condition is satisfied by the chosen fan assembly 303.

The aluminum PCB 305 housing the plurality of UV-C LEDs 304 is a two-layer PCB made with a well-known technology called metal-core PCB, with aluminum being used as the metal. The plurality of UV-C LEDs 304 produce a copious amount of heat, which if not conducted away, would cause damage to the plurality of UV-C LEDs 304 themselves. Traditional FR4 PCBs are not efficient conductors of heat, therefore aluminum core PCBs are used for this type of application. Aluminum is a far better conductor of heat than FR4. Many PCB vendors currently have the capability of making such aluminum core PCBs, such as Bittele (7pcb.com).

The heatsink 301 is designed according to several factors, such as (a) the heat from the plurality of UV-C LEDs 304 that need to be dissipated, (b) air flow capacity of the fan assembly 303, (c) temperature of the ambient air, and (d) maximum temperature that the plurality of UV-C LEDs 304 are allowed to operate at. Size of the heatsink 301; thickness, height and pitch of the fins of the heatsink 301 is determined from the considerations above. In one example, at full power, the 16 UV-C LEDs 304 can dissipate up to 8 Watts of heat, and the temperature of the plurality of UV-C LEDs 304 needs to be kept below 60 degrees C., with the ambient air temperature being up to 35 degrees C. Given the air flow capability of the chosen fan assembly 303, it was determined that the heatsink marketed by Wakefield (wakefield-vette.com) with part number SKV606021-AL would be adequate for this purpose. It comes with a size of 60 mm×60 mm×21 mm, and has thermal resistance of 0.9 degree C./W with forced air convection and 7.9 degree C./W with natural convection. Such calculations to determine the size of the heatsink are done with thermal simulations to which practitioners in the field are well-versed with.

The back of the aluminum PCB 305 needs to make a good thermal contact with the base of the heatsink 301, even when the two are tightly constrained with screws. The thermal contact is provided by spreading a thermal joint compound in the interface between the two. In examples of the present disclosure, the thermal joint compound may be the part number 126-2 of Wakefield (wakefield-vette.com).

One or more temperature sensors 310 are mounted on the aluminum PCB 305 to report the temperature of the aluminum PCB 305. In examples of the present disclosure, the one or more temperature sensors 310 are of a Negative Temperature Coefficient (NTC) type and may be sourced from the part number NTCS0805E3103FHT of Vishay (vishay.com). It has a nominal resistance of 10 k Ohms at 25 degrees C.

FIG. 3 further shows an electronic board 308 mounted to the ceiling wall 201 with screws 204 and spacers 307. The electronic board 308 receives its electrical power in the form of 12V DC from the external power supply 106 through the power cable 311. It supplies and controls the power to the fan assembly 303 through the cable 306 and to the plurality of UV-C LEDs 304 through the cable 309. The cable 309 further provides power to and read the signal from the one or more temperature sensors 310. The electronic board 308 further provides power to and receives signal from the optical flux meter system 414 of FIG. 4 with the cable 312.

In examples of the present disclosure, the electronic board 308 provides a constant DC voltage of 12V to the fan assembly 303. The electronic board 308 further provides a controllable range of average current of 0 to 100 mA to the plurality of UV-C LEDs 304. The electronic board 308 further reads the one or more temperature sensors 310 and interprets the reading into a degree C. temperature reading, representative of the temperature of the plurality of UV-C LEDs.

In examples of the present disclosure, the control algorithm (also referred to as method or process implemented to the electronic circuit 399 of the electronic board 308) implemented in the electronic board 308 for powering the plurality of UV-C LEDs 304 is as follows:

a) Provide constant power to the fan assembly 303 at 12V DC.
b) Provide 20 mA average current to the plurality of UV-C LEDs 304.
c) Measure the temperature T from the one or more temperature sensors 310.
d) If T is greater than or equal to 65 degrees C., reduce the average current to the plurality of UV-C LEDs 304 by 2 mA, subject to a maximum of 100 mA.
e) If T is less than 55 degrees C., increase the average current to the plurality of UV-C LEDs 304 by 2 mA, subject to a minimum of 0 mA.
f) If temperature T is greater than 80 degrees C., decrease the average current to the plurality of UV-C LEDs 304 to 0 mA. Wait for 5 minutes.
g) Wait for 10 seconds. Go to step (b).

The control method is a simple time-step-delay P-(proportional) method. Practitioners in the field of electronic control may find it more appropriate in alternate methods to expand the P-control to the full set or a subset of the comprehensive proportional-integral-derivative (PID) control, and such methods are incorporated into this invention by reference.

FIG. 4 shows a partial, internal view of the housing 102 in examples of the present disclosure. In one example, only one wall 411 contains the viewing port 107 and the one or more apertures 105. All other walls 412 are substantially similar to each other. FIG. 4 depicts the internal placements of UV-C reflector 401, the fluorescent and translucent plate 404 for the viewing port 107, the one or more UV-blocking optical baffles 402, the one or more apertures 105, and the optical flux meter system 414.

Substantial portion of the inside of the wall 411 is covered with a UV-C reflector 401. UV-C reflectors 415 are present on all other walls covering a substantial amount of their surfaces. UV-C Reflector 403 covers a substantial amount of the surface of a floor wall 413 of the housing 102. Together, the reflectors 401, 415 and 403 reflect the photon flux back into the housing air volume rather than allowing the flux being absorbed by the walls. Multiple reflections increase the number of effective UV-C photons available to react and destroy the germs present in the air volume. Most reflecting materials with high reflectivity in visible and even UV-A and UV-B bands do not have high reflectivity as in UV-C band. Therefore, the material must be carefully chosen looking for high UV-C reflectivity for this purpose. In examples of the present disclosure, the reflectors 401, 415 and 403 may be a sheet of expanded poly-tetra-fluoro-ethylene (ePTFE) with a thickness of 0.5 mm from Gore-Tex (gore-tex.com). It has an adhesive backing for easy placement and retention on the inside of the wall.

In examples of the present disclosure, the reflectors 401, 415 and 403 comprise a paint containing at least 10% by volume Barium Sulfate particles with average size less than 0.3 mm. Barium Sulfate is known to have a high reflectance in the wavelength range of UV-C, and is used in other optical applications, such as integrating spheres.

It is desirable to have a safe visual indicator of UV light being present inside the housing volume from outside, while not exposing the outside environment to UV-C photons generated inside the housing. As shown further in FIG. 4, this purpose is solved by a fluorescent and translucent plate 404 pasted on the wall 411 covering the viewing port 107. The fluorescent and translucent plate 404 is made of a piece of acrylic plate of one-eighth inch thickness and is loaded with a fluorescent dye. It fluoresces in bright red color in response to absorbing UV-C light. It receives part of the UV-C flux when the sanitizer is on and generates the bright red fluorescent light. Being translucent, part of the bright red light is visible to the side oriented towards the outside of the housing 102. The fluorescent and translucent plate 404 is glued to the wall 411 covering the viewing port 107, therefore the bright red fluorescent light being visible to the user.

FIG. 4 also shown an optical flux meter system 414 placed on the floor wall 413 of the housing 102. The optical flux meter system 414 comprises a UV-C sensitive photodiode, a biasing and amplifier circuit, an analog-to-digital converter (ADC) and a communication circuit. The incoming UV-C flux from the plurality of UV-C LEDs 304 is measured with the optical flux meter system 414. The measurement is then reported to the electronic board 308 via the cable 312. The optical flux meter system 414 is also powered from the electronic board 308 via the cable 312.

It is known that the optical efficiency of a light generator, defined as the ratio of optical power produced in the UV-C band to electrical power consumed, gets degraded in all UV light generators, including the plurality of UV-C LEDs 304, over the time of service. It is not possible to detect such degradation by measuring just the electrical power consumed. It is therefore desirable to measure the optical power of the plurality of UV-C LEDs 304 with the optical flux meter system 414, such that the actual UV-C optical power in the internal volume of the housing 102 is reliably measured. The user may be alerted to such degradation and in turn can decide to replace the parts or the entire device since otherwise the air sanitizer would become less and less effective over time.

Figure 7:
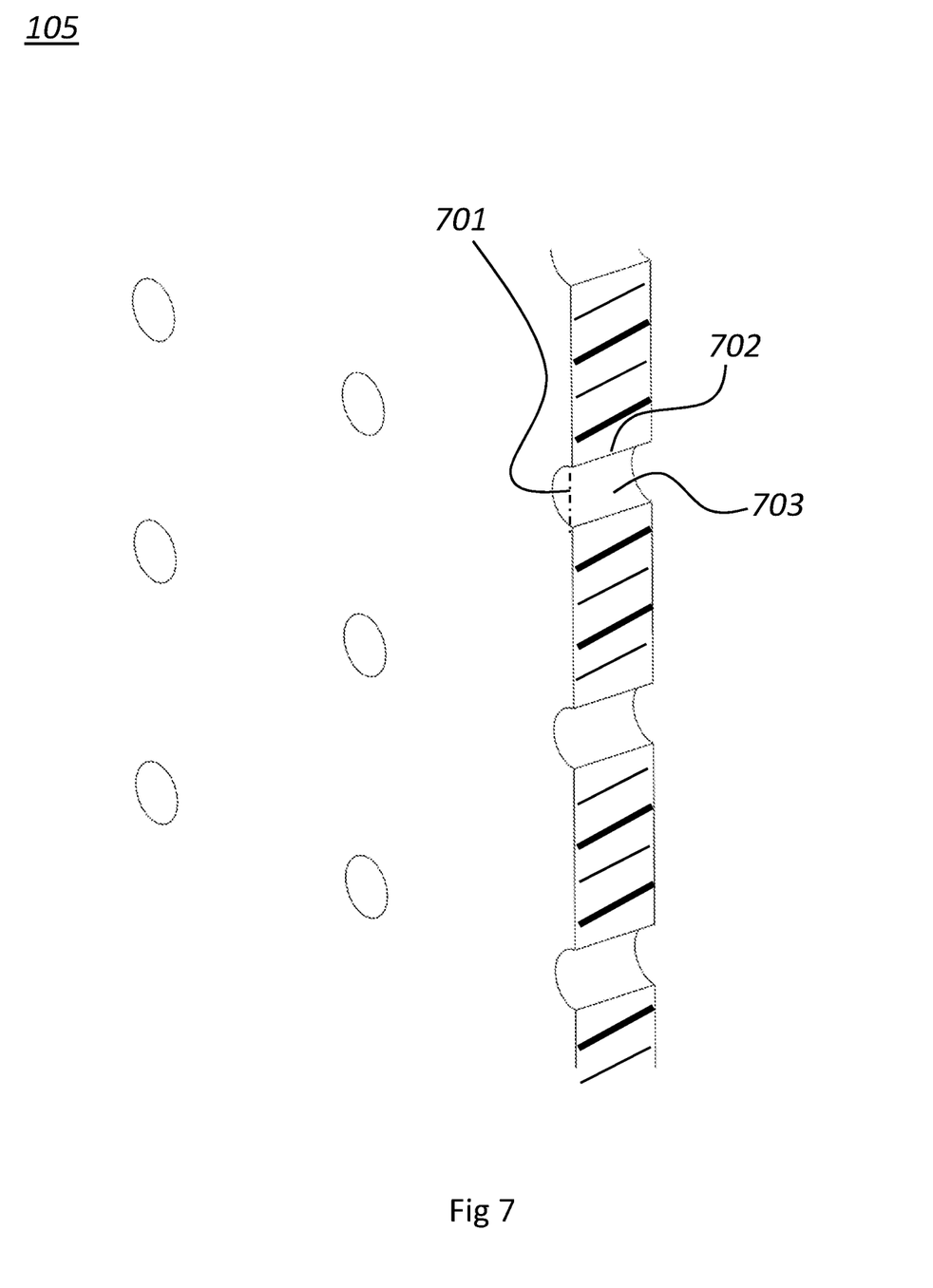
FIG. 7 shows a partial cross-sectional view along AA' of FIG. 1 of apertures in examples of the present disclosure.

Referring now to FIG. 7, the one or more apertures 105, are designed to expel the sanitized air from inside the housing 102 to the outside environment while minimizing the leakage of UV-C light flux escaping to the outside environment at the same time. Each individual aperture of the one or more apertures 105 has a geometric dimension relative to the direction of outgoing UV-C photons such that average diameter 701 of the aperture is less than one-third of the average length 702 of the aperture. The inside surface 703 of the one or more apertures 105 is coated with a coating that absorbs more than 80% of UV-C photons incident upon it. In examples of the present disclosure, the coating comprises more than 2% by volume of carbon particles of average diameter less than 50 microns in a paint medium. In examples of the present disclosure, the inside surface 503 is spray painted with the commercial carbon loaded paint from MG Chemicals (mgchemicals.com) with part number 838AR.

Although the coated one or more apertures 105 absorb more than 80% of UV-C light flux that attempt to cross them, another layer of protection against the leakage of UV-C light to outside environment is desired. Such a method of protection is described in FIG. 4. The one or more UV-absorbing optical baffles 402 is glued to the wall 411 covering the one or more apertures 105.

Figure 6:
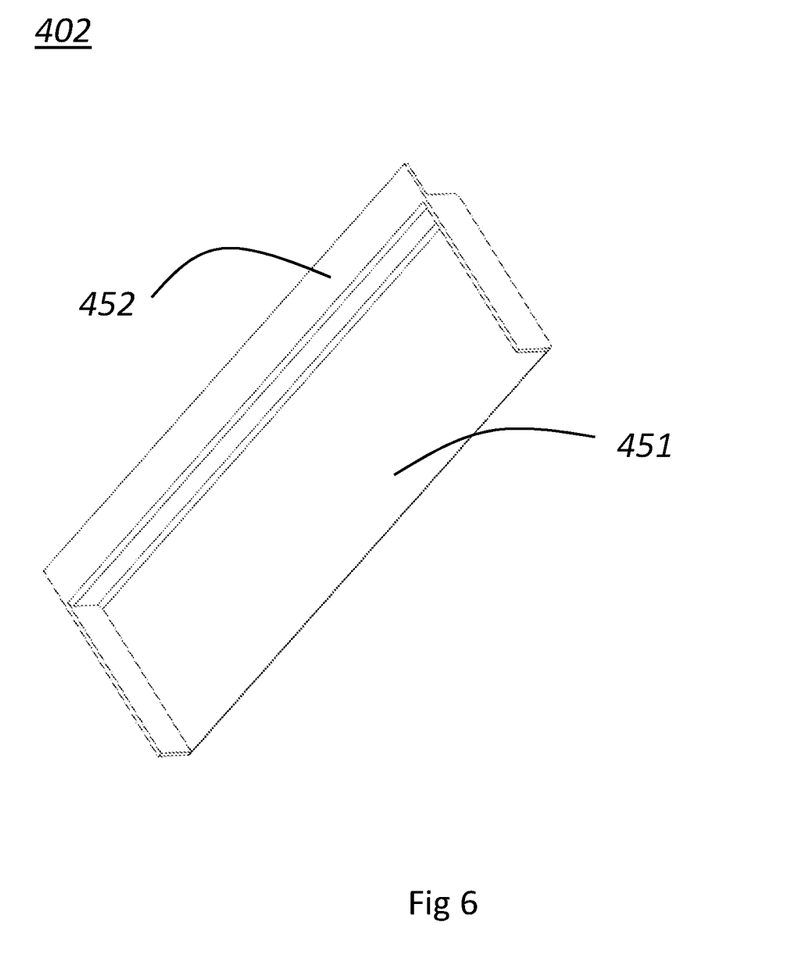
FIG. 6 shows a UV-absorbing optical baffle in examples of the present disclosure.

FIG. 6 shows one of the one or more UV-absorbing optical baffles 402 in examples of the present disclosure. Each of the one or more UV-absorbing optical baffles 402 has a lip 452, which is glued to the wall 411. The interior surface 451 is painted with the same material as the inside surface 703 of the one or more apertures 105.

Each of the one or more UV-absorbing optical baffles 402, due to it geometric shape, substantially blocks the UV coming from the plurality of UV-C LEDs 304. The small fraction of UV-C photons that still make it into the baffle volume are substantially absorbed by the UV-absorbing coating on the surface 451. Beyond that, any remaining UV-C leakage entering the one or more apertures 105 is substantially absorbed due to its geometry and UV-absorbing coating. Thus, any leakage of UV-C light to the outside environment is practically eliminated.

Figure 5:
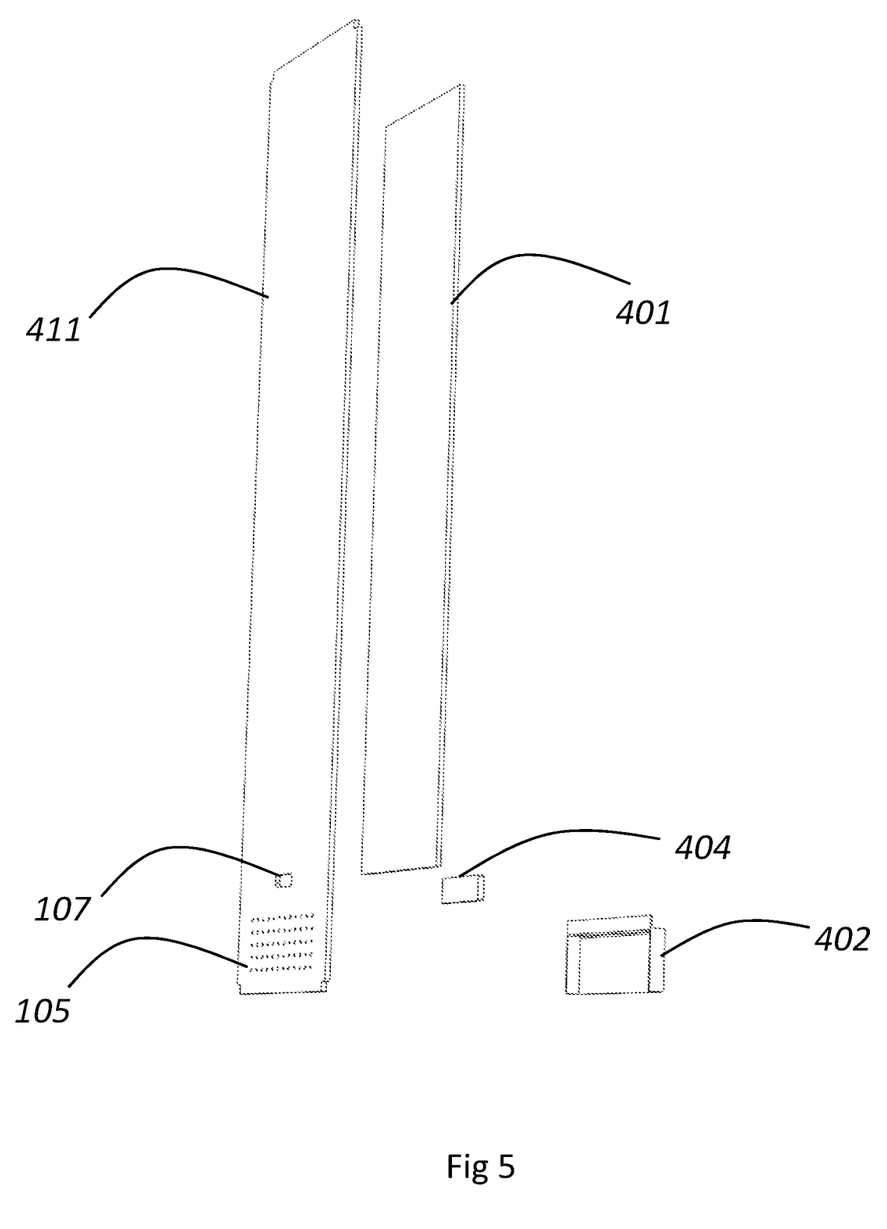
FIG. 5 is an exploded plot of a reflector, a fluorescent and translucent plate, one or more UV-absorbing optical baffles, and a wall of the housing of FIG. 1 in examples of the present disclosure.

FIG. 5 is an exploded plot of the reflector 401, the fluorescent and translucent plate 404, the one or more UV-absorbing optical baffles 402, the wall 411 containing the viewing port 107 and the one or more apertures 105.

Figure 8:
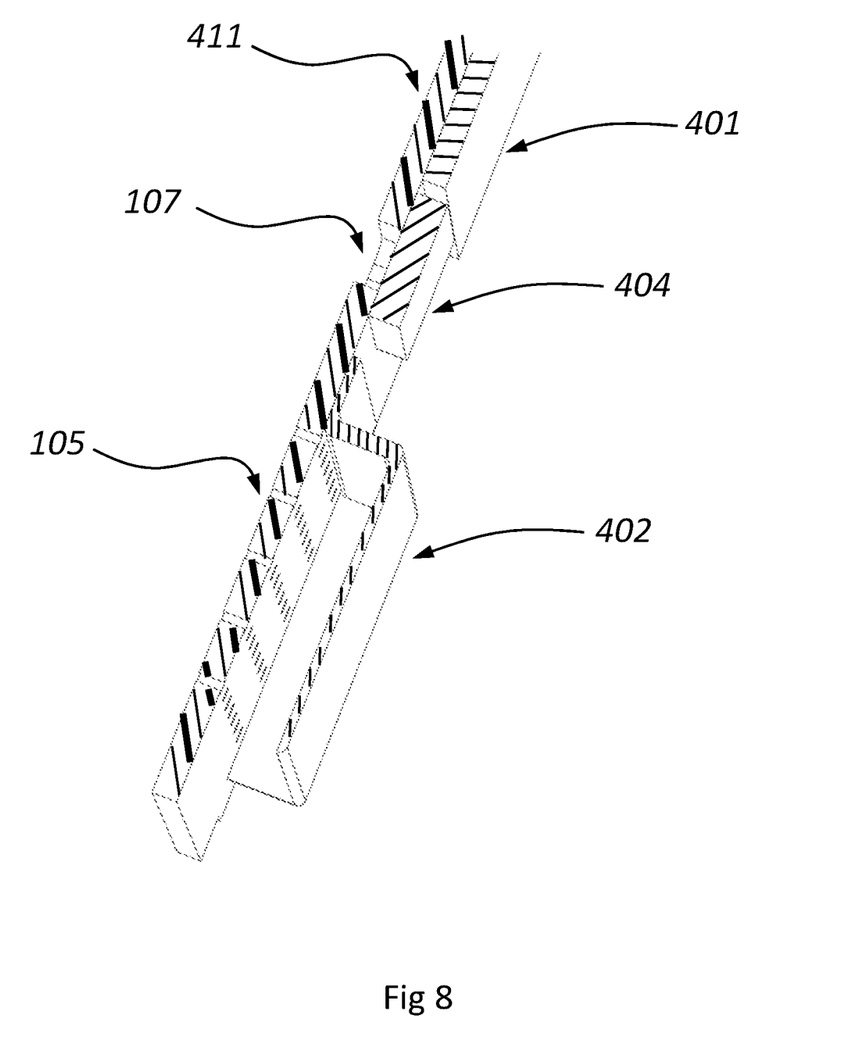
FIG. 8 shows a partial cross-sectional view along AA' of FIG. 1 of a wall of the housing of FIG. 1, one or more apertures, a viewing port, a fluorescent plate, a UV-absorbing optical baffle and a UV reflector in examples of the present disclosure.

FIG. 8 shows a partial cross-sectional view along AA' of FIG. 1 of the wall 411 of the housing 102 of FIG. 1, the one or more apertures 105, the viewing port 107, the fluorescent and translucent plate 404, one of the one or more UV-absorbing optical baffles 402 and a UV reflector 401 in examples of the present disclosure.

Those of ordinary skill in the art may recognize that modifications of the embodiments disclosed herein are possible. For example, a total number of LEDs mounted on the PCB may vary. Other modifications may occur to those of ordinary skill in this art, and all such modifications are deemed to fall within the purview of the present invention, as defined by the claims.

The invention claimed is:
1. An air sanitizer comprising:
a housing;
a heatsink;
a printed circuit board (PCB) attached to the heatsink;

a plurality of ultraviolet C light emitting diodes (UV-C LEDs) attached to the PCB;

one or more temperature sensors monitoring temperature of the heatsink or temperature of the PCB;

an electronic circuit supplying and controlling electrical power to the plurality of UV-C LEDs based on a predetermined optical power level and temperature output values of the one or more temperature sensors, and reporting a status of the air sanitizer to a user;

a fan assembly drawing external air into the housing for cooling the heatsink;

a layer of UV-reflective material in the housing, the layer of UV-reflective material facilitating a plurality of reflections of UV-C light so as to improve utilization of the UV-C light;

one or more apertures at a downstream of the housing so as to expel sanitized air;

one or more UV-blocking optical baffles covering the one or more apertures; and an optical flux meter system in the housing, the optical flux meter system being in a path of the UV-C light emitted from the plurality of UV-C LEDs.

2. The air sanitizer of claim 1, wherein the plurality of UV-C LEDs have at least 20% of optical power of emission spectrum with wavelength less than 280 nanometers.

3. The air sanitizer of claim 1, wherein the layer of UV-reflective material is a sheet of expanded poly-tetra-fluoro-ethylene (ePTFE).

4. The air sanitizer of claim 1, wherein the layer of UV-reflective material is a white paint containing at least 10% by volume Barium Sulfate particles with average size less than 0.3 mm.

5. The air sanitizer of claim 1, wherein the one or more UV-blocking optical baffles transmit less than 0.01% of the UV-C light emitted from the plurality of UV-C LEDs in a wavelength range from 200 nm to 280 nm.

6. The air sanitizer of claim 1, wherein each of the one or more UV-blocking optical baffles is a plastic shroud coated with a UV-absorbing paint.

7. The air sanitizer of claim 1, wherein the fan assembly comprises a fan or a blower and a replaceable filter.

8. The air sanitizer of claim 1, wherein the electronic circuit comprises a power supply converting an external supply voltage level to a constant average current determined by the user.

9. The air sanitizer of claim 1, wherein the electronic circuit implements a control architecture by reducing current to the plurality of UV-C LEDs when the temperature output values of the one or more temperature sensors increase so that the temperature of the heatsink is constantly under a first pre-determined temperature threshold or the temperature of the PCB is constantly under a second pre-determined temperature threshold.

10. The air sanitizer of claim 9, wherein the control architecture of the electronic circuit is implemented with a proportional-integral-derivative) (PID) control technique.

11. The air sanitizer of claim 1, wherein the housing comprises a plurality of walls and at least one viewing port on the plurality of walls and wherein the at least one viewing port allows the user to monitor presence of the UV-C light within the housing.

12. The air sanitizer of claim 11, wherein the at least one viewing port comprises an aperture blocked with a translucent and fluorescent plate; wherein fluorescence is generated in response to the presence of the UV-C light within the housing; and wherein a part of the fluorescence is visible outside the housing and serves as an optical indicator of the presence of the UV-C light within the housing.

13. The air sanitizer of claim 12, wherein the translucent and fluorescent plate is made of an acrylic material doped with a fluorescent dye.

14. The air sanitizer of claim 1, wherein the optical flux meter system comprises a photodiode, an amplifier, a signal conditioning circuit, an analog-to-digital (ADC) converter, and a communication circuit.

15. The air sanitizer of claim 14, wherein the photodiode has more than 50% relative spectral response integrated in a spectral range of a UV-C band of 200-280 nm.

16. The air sanitizer of claim 14, wherein the photodiode is made of a zinc-oxide and diamond material.

17. The air sanitizer of claim 1, wherein the electronic circuit powers the optical flux meter system; and wherein the electronic circuit receives light flux reading from the optical flux meter system.

18. The air sanitizer of claim 1, wherein the electronic circuit contains a microprocessor, a memory, a reporting system, and an implemented method that compares a current UV light measurement with historic UV light readings and reports through the reporting system a degradation of the air sanitizer when the current UV light measurement is less than a first UV light reading at a starting of service by a pre-determined light threshold.

19. The air sanitizer of claim 18, wherein the reporting system comprises transmitting values representing the status of the air sanitizer:

through a visual display including a liquid crystal display (LCD) panel or an LED panel;

through a wireless communication including a WiFi network or a Bluetooth network, to an external computing device for display, analysis and archival purpose; or through a wired communication including an RS-232 interface or a CANBus interface, to the external computing device for display, analysis and archival purpose.

20. The air sanitizer of claim 1, wherein a length direction of each of the one or more apertures is parallel to an outgoing direction of a plurality of UV-C photons; and wherein an average diameter of the one or more apertures is less than one-third of an average length of the one or more apertures.

21. The air sanitizer of claim 20, wherein a respective circumferential surface of each of the one or more apertures is coated with a coating that absorbs more than 80% of the plurality of UV-C photons incident upon the respective circumferential surface.

22. The air sanitizer of claim 21, wherein the coating of the one or more apertures comprises more than 10% by volume of carbon particles of average diameter less than 50 microns in a paint medium.

* * * * *